US012447041B2

(12) United States Patent
Brennan et al.

(10) Patent No.: US 12,447,041 B2
(45) Date of Patent: Oct. 21, 2025

(54) COLLECTING DEVICE

(71) Applicant: EAKIN R&D LIMITED, Comber County Down (GB)

(72) Inventors: Nathan Brennan, Comber County Down (GB); Benjamin Derek Mahood, Comber County Down (GB); Sebastian Miller, Comber County Down (GB)

(73) Assignee: EAKIN R&D LIMITED, Comber County Down (GB)

(*) Notice: Subject to any disclaimer, the term of this patent is extended or adjusted under 35 U.S.C. 154(b) by 458 days.

(21) Appl. No.: 17/800,807

(22) PCT Filed: Feb. 22, 2021

(86) PCT No.: PCT/GB2021/050438
§ 371 (c)(1),
(2) Date: Aug. 18, 2022

(87) PCT Pub. No.: WO2021/165703
PCT Pub. Date: Aug. 26, 2021

(65) Prior Publication Data

US 2023/0091863 A1 Mar. 23, 2023

(30) Foreign Application Priority Data

Feb. 20, 2020 (GB) .................................... 2002407

(51) Int. Cl.
*A61F 5/449* (2006.01)
*A61F 5/44* (2006.01)

(52) U.S. Cl.
CPC ........... *A61F 5/449* (2013.01); *A61F 5/4404* (2013.01)

(58) Field of Classification Search
CPC ........ A61F 5/449; A61F 5/4404; A61F 5/443; A61F 5/4407; A61F 5/445; A61F 5/4405; Y10T 156/10
See application file for complete search history.

(56) References Cited

U.S. PATENT DOCUMENTS

| | | | | |
|---|---|---|---|---|
| 2008/0300556 | A1 | 12/2008 | Fenton | |
| 2014/0039430 | A1 | 2/2014 | Richmann et al. | |
| 2014/0163497 | A1* | 6/2014 | Hannan | A61F 5/443 156/60 |
| 2015/0320585 | A1* | 11/2015 | Fattman | A61F 5/443 604/344 |
| 2018/0333290 | A1* | 11/2018 | Jones | A61F 5/443 |

* cited by examiner

*Primary Examiner* — Rebecca E Eisenberg
*Assistant Examiner* — Rachel O'Connell
(74) *Attorney, Agent, or Firm* — Dinsmore & Shohl LLP

(57) ABSTRACT

A collection pouch for bodily fluids/waste has a plurality of flexible polymer film layers. At least two layers form a collecting bag for containing bodily fluids/waste, with front and rear walls formed from the film layers. An opening is formed in the rear wall of the bag for receiving bodily fluids/waste. A flexible material cover covers the collecting bag and a peripheral bonding seam extends along an upper edge the apparatus that bonds at least part of the bag and cover together. One or more strengthening elements are formed by a region of bonding between a film layer at the upper end of the pouch and the cover. The strengthening elements are at the upper end of the pouch inwardly of the peripheral bonding seam and strengthen the upper section to maintain the shape of the upper end of the pouch and inhibit sagging as the collecting bag is filled.

20 Claims, 8 Drawing Sheets

COLLECTING DEVICE

CROSS-REFERENCE TO RELATED APPLICATIONS

This application is the U.S. National Stage of PCT/GB2021/050438 filed on Feb. 22, 2021, which claims priority to United Kingdom Patent Application 2002407.1 filed on Feb. 20, 2020, the entire content of both are incorporated herein by reference in their entirety.

FIELD OF THE INVENTION

The present invention relates to a collecting device and in particular an ostomy pouch having strengthening zones for structurally reinforcing the pouch.

BACKGROUND OF THE INVENTION

Ostomy procedures such as colostomy, ileostomy and/or urostomy, result in a portion of the patient's ileum or colon protruding through an opening in the patient's abdomen. The protruding end section of the ileum or colon is referred to as a stoma. Following an ostomy procedure, a collection device is required for collecting waste from the patient's stoma, which may be urine or faeces depending on the ostomy procedure and the nature of the stoma. Typically, a collection bag or 'ostomy pouch' is provided that receives the stoma and collects the waste.

Ostomy pouches consist generally of a collecting bag comprising two sheets of flexible impermeable plastic film that form front and rear walls that are welded together around their periphery to form a common edge seal. The collecting bag will include an inlet for receiving the stoma and will typically also be provided with a drainage system to enable the pouch to be periodically emptied by the patient as it fills. A mounting plate is provided for mechanically securing the ostomy pouch to the body of the wearer. The mounting plate is secured to the collecting bag and has an aperture that defined the inlet opening of the pouch.

The plastic film forming the collecting bag is typically transparent, such that the contents of the pouch are visible through the film walls. It is generally undesirable for the contents of the pouch to be visible during normal use. In addition, the plastic film of the collecting bag can be uncomfortable if held in direct contact with the wearer's skin. In order to preserve wearer dignity and improve comfort it is known to provide pouch covers, typically formed from a fabric material, to obscure the contents of the plastic collecting bag and provide a barrier or 'comfort' layer between the collecting bag and the wearer's skin. The pouch cover is typically bonded to the collecting bag about a common peripheral edge, such as by thermal welding, to form a narrow, laminated seam.

As the collecting bag fills during use, the weight of the contents can cause sagging of the pouch. As the load in the collecting bag increases the lower part of the pouch begins to pull down on the upper part, causing the upper part to sag downwards and sag or fold forwards. The edge seams of the lower part of the pouch begin to kink and buckle, which can cause uneven distribution of the load within the collecting bag. As a result, the load on the mounting plate may become unevenly distributed, pulling down more on one side than the other, which can cause discomfort. The kinked seam may also extend rearwardly into contact with the wearer's skin, which may also cause discomfort due to the stiffness of the seam. Deformation of the pouch can therefore cause discomfort to the wearer and produce an unsightly appearance, with the pouch become more noticeable beneath the wearer's clothing as it sags and folds.

It is therefore desirable to provide an improved ostomy pouch which addresses the above described problems and/or which offers improvements generally.

SUMMARY OF THE INVENTION

According to the present invention there is provided an ostomy pouch as described herein.

In one aspect of the invention there is provided a collecting apparatus for bodily fluids or bodily waste comprising a plurality of flexible polymer film layers. At least two of the flexible polymer film layers form a collecting bag for containing bodily fluids or bodily waste, the collecting bag comprising front and rear walls formed from said at least two flexible polymer film layers. An opening in the rear wall of the collecting bag is provided for receiving bodily fluids or bodily waste. A flexible material cover at least partially covers the collecting bag. A peripheral bonding seam extends along at least an upper edge the apparatus that bonds at least part of the collecting bag and the cover together. One or more strengthening elements are formed by a region of bonding between one or more of the flexible polymer film layers and the flexible material cover. The one or more strengthening elements are arranged at the upper end of the apparatus inwardly of the peripheral bonding seam and are configured to strengthen the upper section of the apparatus to maintain the shape of the upper section and inhibit sagging as the collecting bag is filled in use.

The strengthening zones advantageously provide structural support, in addition to the upper peripheral bonding seam, that resist sagging or bulging of the collecting bag as the weight of the lower part of the bag begins to pull downwardly as it fills. Preventing sagging and maintaining the form of the pouch enhances the ability of the pouch to remain as discrete as possible beneath a wearer's clothes.

At least one of the one or more strengthening elements preferably has a shape that conforms to the shape of the peripheral bonding seam at the upper end of the apparatus, thereby supporting and reinforcing the original shape of the pouch.

The upper end of the apparatus has a convex curved shape, meaning it curves upwardly at the upper end of the pouch, and the at least one strengthening element has a correspondingly curved shape, with the at least one strengthening element being located immediately beneath the upper peripheral seam.

The at least one strengthening element may have an elongate arcuate shape that is concentric with the upper peripheral seam.

The at least one strengthening element may extend substantially parallel to the curved upper peripheral edge of the apparatus.

The at least one strengthening element may have a substantially semi-circular shape with a curved upper edge that extends substantially parallel to the curved upper peripheral edge of the apparatus.

The flexible material cover preferably comprises a front part arranged on a first side of the collecting bag that in use faces forward away from the wearer, the front part consists of an upper cover section and a lower cover section, the upper cover section is formed of at least one flexible material layer and at least one flexible polymer film layer that are bonded together to form the one or more strengthening elements.

The flexible cover layer may also comprise a rear part on the opposing side of the collecting bag.

At least one of the one or more strengthening elements extending across the upper section of the collecting apparatus may be spaced inwardly from the peripheral bonding seam such that a gap is defined therebetween that is spanned by an unbonded portion of the flexible material layer and the intermediate polymer layer.

The lower cover section may include a viewing window through which the opening of the collecting bag is visible and the upper cover section forms a flap that is reconfigurable between a closed configuration in which at least part of the upper cover section covers the viewing window and the opening is obscured, and an open configuration in which the viewing window is uncovered and the opening is visible.

The upper cover section preferably comprises an outer flexible material layer and an intermediate flexible polymer film layer located between the outer flexible material layer and the collecting bag, and the one or more strengthening elements are formed by regional bonding between the outer flexible material layer and the intermediate flexible polymer film layer.

The upper cover section may have an outer peripheral edge that is bonded with and forms part of the peripheral bonding seam and a lower edge located inboard of the outer peripheral edge at least part of which extends across the apparatus below the level of the window, wherein the outer flexible material layer and the intermediate polymer film layer are bonded along the lower edge to form a strengthening zone that stiffens the lower edge and maintain its form in the open and closed configurations.

The upper cover section may further comprise an inner flexible material layer located on the opposing side of the intermediate flexible polymer film layer to the outer flexible material layer and the one or more strengthening elements are formed by a region of bonding between the outer flexible material layer, inner flexible material layer and intermediate flexible polymer film layer.

A plurality of strengthening zones may be provided, wherein the upper cover section has a width extending across the apparatus and a length extending vertically along the apparatus, and at least one of the strengthening elements is an elongate element extending lengthwise along part of the upper cover section inboard of the outer peripheral edge to stiffen the upper cover section and maintain its form in the open and closed configurations.

Preferably, a portion of the upper cover section folds about a lateral fold line to reconfigure the upper cover section between the open and closed configurations and the one or more strengthening zones are arranged such that they are not located on or across the fold line, meaning that while the strengthening zone may extend across the fold line, there is no bonding between the layers along the fold line itself.

Preferably a portion of the upper cover section folds about a lateral fold line to reconfigure the upper cover section between the open and closed configurations and the one or more elongate strengthening elements arranged lengthwise along the upper cover section include a split line or weakened section located at the fold line to facilitate folding of the upper cover section. A split line is any break in the strengthening element such that there is no bonding between layers on the fold line.

The upper cover section preferably has a lower part located below the fold line in the closed configuration that folds upwardly about the fold line to the open configuration. The lower part preferably tapers inwardly to its lowermost point, such that it has a substantially v-shaped form.

The curved uppermost strengthening element may define a first strengthening element and the vertical or lengthwise strengthening elements may comprise arms extending downwardly from the ends of the first strengthening element. The arms are preferably arranged parallel with the side edges of the lower part of the upper cover section, such that they are angled inwardly towards the longitudinal centreline of the pouch. The upper ends of the arms may be spaced from the outer end of the first strengthening element to define a split line that is arranged on the fold line.

In an embodiment of the invention there is provided an ostomy pouch a collecting apparatus for bodily fluids or bodily waste comprising a collecting bag for containing bodily fluids or bodily waste. The collecting bag comprises front and rear walls formed from a flexible polymer film. An opening is formed in the rear wall of the collecting bag for receiving bodily fluids or bodily waste. A flexible material cover at least partially covers the collecting bag. The cover comprises a front part arranged on a first side of the collecting bag that in use faces forward away from the wearer and a rear part on the opposing side of the collecting bag that in use is located between the collecting bag and the wearer. A peripheral bonding seam is formed along which the front and rear parts of the cover and the front and rear walls of the collecting bag are bonded together. One or more strengthening zones are provided having at least a portion thereof located inboard of the peripheral bonding seam. The front and rear parts of the cover and the front and rear walls of the collecting bag are bonded together to form the one or more strengthening zones for providing the pouch with structural reinforcement. The term "bonded" means any form of securing the layers together by means of adhesive, heat, pressure or by chemical bonds, which may comprise welding such as thermal or RF welding, adhesives, or by any other suitable means.

Conventionally the collecting bag and outer cover of collection pouches such as ostomy pouches are only bonded together only along a thin peripheral seam suitable for closing and sealing the edge of the pouch. Bonding these layers together in other regions inboard of the peripheral seam, while not necessary to close and seal the bag in addition to the peripheral seam, provides strengthening zones that structurally reinforce and support the pouch in use. These strengthening zones may for example support the bag and prevent sagging and/or assist in optimising distribution of load of the contents within the collection bag. Forming the strengthening zones by bonding each of the front and rear parts of the cover and the front and rear walls of the collecting bag together in a lamination of at least 4 layers provides significantly improved structural support.

The cover may be formed from a woven or unwoven fabric material to provide a comfort layer over the collecting bag.

Preferably the one or more strengthening zones comprise a first strengthening zone arranged at the periphery of the pouch that is integrally formed as part of the peripheral bonding seam, wherein the peripheral bonding seam has a first width w1 and the first strengthening zone has a width w2 that is greater than the width w1 and is arranged such that a portion the first strengthening zone extends inwardly of the peripheral bonding seam. The width is defined as the distance inwardly from the peripheral edge in a direction substantially perpendicular to the peripheral edge.

The collecting apparatus includes a longitudinal central axis extending along its length and preferably further comprises a second strengthening zone arranged at the periphery of the pouch that is integrally formed as part of the peripheral bonding seam, wherein the second strengthening zone has a width w2 and is arranged such that a portion the second strengthening zone extends inwardly of the peripheral bonding seam, wherein the first and second strengthening zones are arranged at the lower end of the pouch on opposing sides of the longitudinal central axis. The second strengthening zone cooperates with the first strengthening zone to support the pouch.

Preferably the first and second strengthening zones have a curved profile defining lobes extending from the bonding seam. The curved shape of the lobes is configured such that under loading the lobes kink forwardly and avoid contact with the wearer. The curvature of the strengthening zones is substantially symmetrical bell-shaped curve. The curvature of the strengthening zones preferably transitions from negative, to positive at the apex and back to negative.

Preferably a curved valley section or bowl is defined between the first and second strengthening zones. The valley section has a radius or curvature that is less than the radius of curvature of the lower edge of the bag, meaning it is steeper sided. The valley section channels or funnels the contents of the collecting bag to towards the centre and ensures that the load is centrally distributed to prevent uneven loading on the mounting plate. At least part of the curvature of the valley section is defined by the curved edges of the strengthening zones.

The collecting apparatus preferably has a curved lower edge and the first and second strengthening zones are located along the curved lower edge and are symmetrically arranged either side of the centreline. The first and second strengthening zones are preferably located along the curved edge between 15 and 35 degrees from the centre line.

The first and second strengthening zones are preferably located within the lower 25% of the total length of the pouch.

The collecting apparatus is preferably an ostomy pouch and the opening in the rear wall of the collecting bag is a stoma opening for receiving a stoma.

The front part of the cover may comprise an upper cover section formed of inner and outer flexible material panels and an intermediate flexible polymer film, wherein the upper cover section has an outer peripheral edge that is bonded in the peripheral bonding seam and lower edge located inboard of the outer peripheral edge.

The inner and outer flexible material panels and intermediate flexible polymer film may be bonded together to form an elongate strengthening zone arranged at the upper end of the upper cover section extending parallel with the peripheral bonding seam and spaced inwardly thereof to strengthen the upper end of the collecting apparatus.

The inner and outer flexible material panels and intermediate flexible polymer film may be bonded together to form a strengthening zone extending along at least part of the lower edge of the upper panel section to strengthen the lower edge and maintain the form of the upper cover section in use.

The upper panel section preferably includes a flap portion that is reconfigurable between a closed position in which the flap covers an underlying part of the collecting apparatus and an open configuration in which the flap exposes said underlying part, wherein the lower edge forms part of the flap section and the strengthening zone extending along the lower edge supports the flap section in the open configuration as well as maintaining the form of the flap in the closed position to prevent undesired exposure of the underlying collection bag. The lower section of the cover may comprise a cut away section or aperture defining a window for viewing the stoma opening through the collection bag and/or for viewing the conente of the bag, and the upper cover section may define a flap for covering the window in a first lowered configuration and revealing the window in a raised configuration.

In another aspect of the invention there is provided a cover for a collecting apparatus for bodily fluids or bodily waste comprising a collecting bag for containing bodily fluids or bodily waste. The collecting bag may comprise front and rear walls formed from a flexible plastic film. An opening is provided in the rear wall of the collecting bag for receiving bodily fluids or bodily waste. Front and rear cover sections are provided that are formed of a flexible material, the front part being arranged in use on a first side of the collecting bag that faces forward away from the wearer and the rear part is arranged in use on the opposing side of the collecting bag between the collecting bag and the wearer. At least one intermediate polymer film layer is located between the front and rear cover sections. A peripheral bonding seam is provided along which the front and rear parts of the cover and the intermediate layer are bonded together. One or more strengthening zones are located inboard of the peripheral bonding seam in which the front and rear cover sections and the least one intermediate layer are bonded together to provide the cover with structural reinforcement.

BRIEF DESCRIPTION OF THE DRAWINGS

The present invention will now be described by way of example only with reference to the following illustrative figures in which.

DESCRIPTION OF THE PREFERRED EMBODIMENTS

Figure 1:
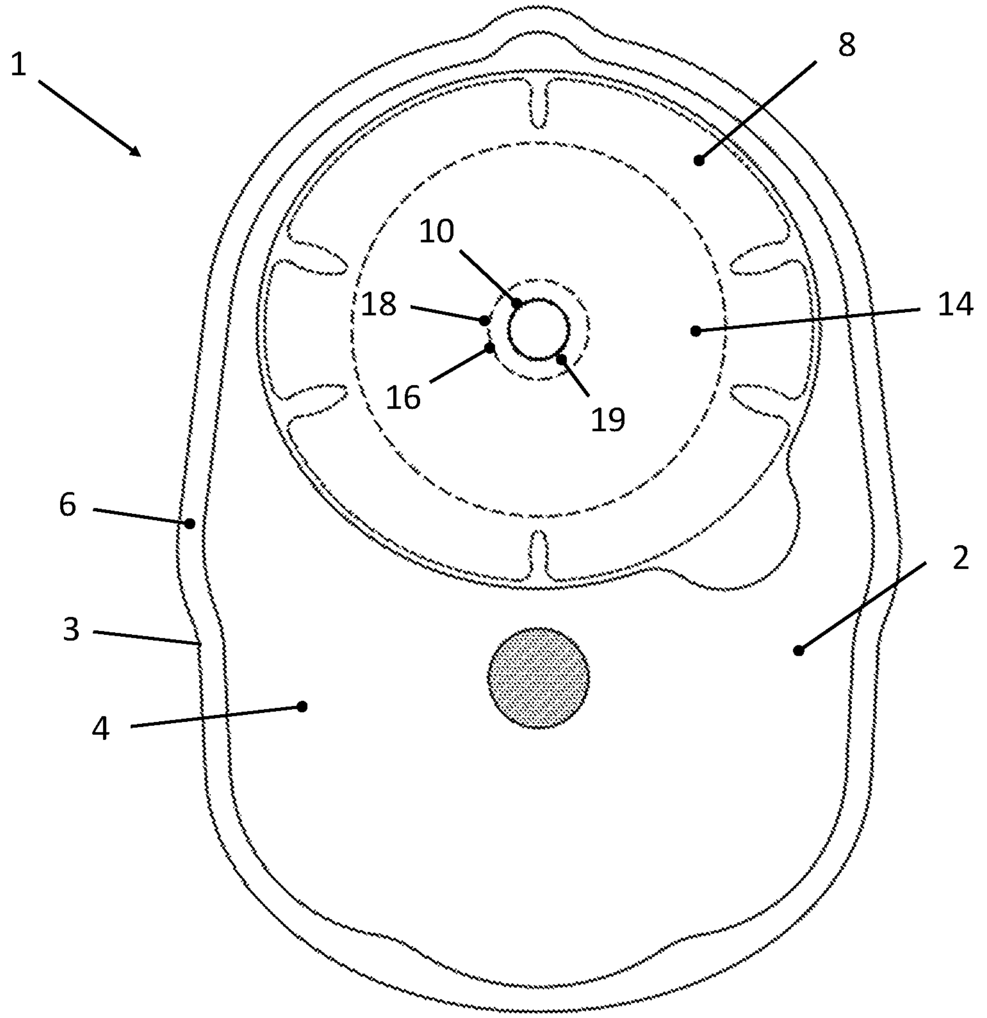
FIG. 1 is a rear view of an ostomy pouch according to an embodiment of the present invention.

Referring to FIG. 1, there is provided an ostomy pouch 1 including a sealed waterproof collecting bag 2 formed from two opposing films of flexible impermeable material. The collecting bag 2 is preferably formed from a plastics material known in the art for forming ostomy pouches and may be a multiple ply film, although it will be appreciated that other suitable materials could be used. The two opposing films define a front wall 3 and a rear wall 4. The front wall 3 and rear wall 4 are sealed along their common peripheral edges 6 to form a receptacle for receiving liquid and solid waste. The peripheral edges 6 may be sealed by welding such as thermal or RF welding, bonded such as by adhesion, or by any other suitable means.

A mounting plate or flange 8 is provided for mechanically securing the ostomy pouch 1 to the body of the wearer. The mounting plate 8 is secured to the rear wall 4 of the collecting bag 2. The flange 8 is an adhesive wafer comprising a foam disc and a hydrocolloid skin barrier layer, which are adhered together to form a flexible adhesive pad. The flange 8 may be a flat disc or may include a convex central portion. Where the mounting flange 8 includes a convex central portion, it may further include a plastic mounting plate which provides a stiffer substrate to which the foam and hydrocolloid layers conform, enabling the convex profile to be maintained.

The rear wall 4 of the collecting bag 2 is sealed to the front face of the mounting flange 8 at a bonding region 14. The term 'front' as used herein refers to a surface which in use faces away from the body of the user, and the term 'rear' refers to a surface which in use faces towards the body of the wearer. The terms 'upper', 'lower', 'top' and 'bottom' as used herein relate to the pouch as oriented on the wearer in use. The flange 8 includes an aperture 10 arranged substantially centrally on the mounting flange 8. The bonding region 14 is annular and surrounds the aperture 10. A corresponding aperture 16 is formed in the rear wall 4 with an edge 18 to which the inner edge of the sealing region 14 extends such that the rear wall 4 is sealed to the mounting plate 8 around the entire periphery of the aperture 16. A region 19 of the flange 8 extends radially inwards from the inner edge 18 of the aperture 16 to the edge of the aperture 10.

The aperture 16 defines stoma inlet opening into the collecting bag 2 through which the wearer's stoma is extended in use. The flange 8 surrounds the stoma in use. The size stoma inlet 10 is able to be selectively increased by cutting the mounting plate 8, and guide lines may be printed on the mounting plate for openings of increasing diameter to assist in accurate cutting of the stoma inlet 10. The bonding layer 14 is sized to be larger than the maximum stoma inlet size so there is always of region of bonding between the bag 2 and the mounting plate 8 that surrounds and seals the stoma opening 10. The hydrocolloid adhesive layer at the rear surface of the flange 8 provides a barrier seal with the wearer's skin extending from the peripheral edge 18 of the mounting plate 8 to the stoma inlet 10. In this way, when the stoma is extended through the stoma inlet 10 in use a barrier seal is created between the mounting plate 8 and the skin of the wearer that is airtight and watertight from the edge of the stoma inlet 10 outwardly, thereby sealing the contents of the collecting bag 2 from the external environment.

The flange 8 is arranged at the upper end of the pouch 1 such that when the pouch 1 is arranged vertically in use a significant portion of the volume of the collecting bag 2 is arranged beneath the opening 10. In use, waste from the stoma passed directly into the volume of the collecting bag 2 beneath the stoma inlet 10.

Figure 2:
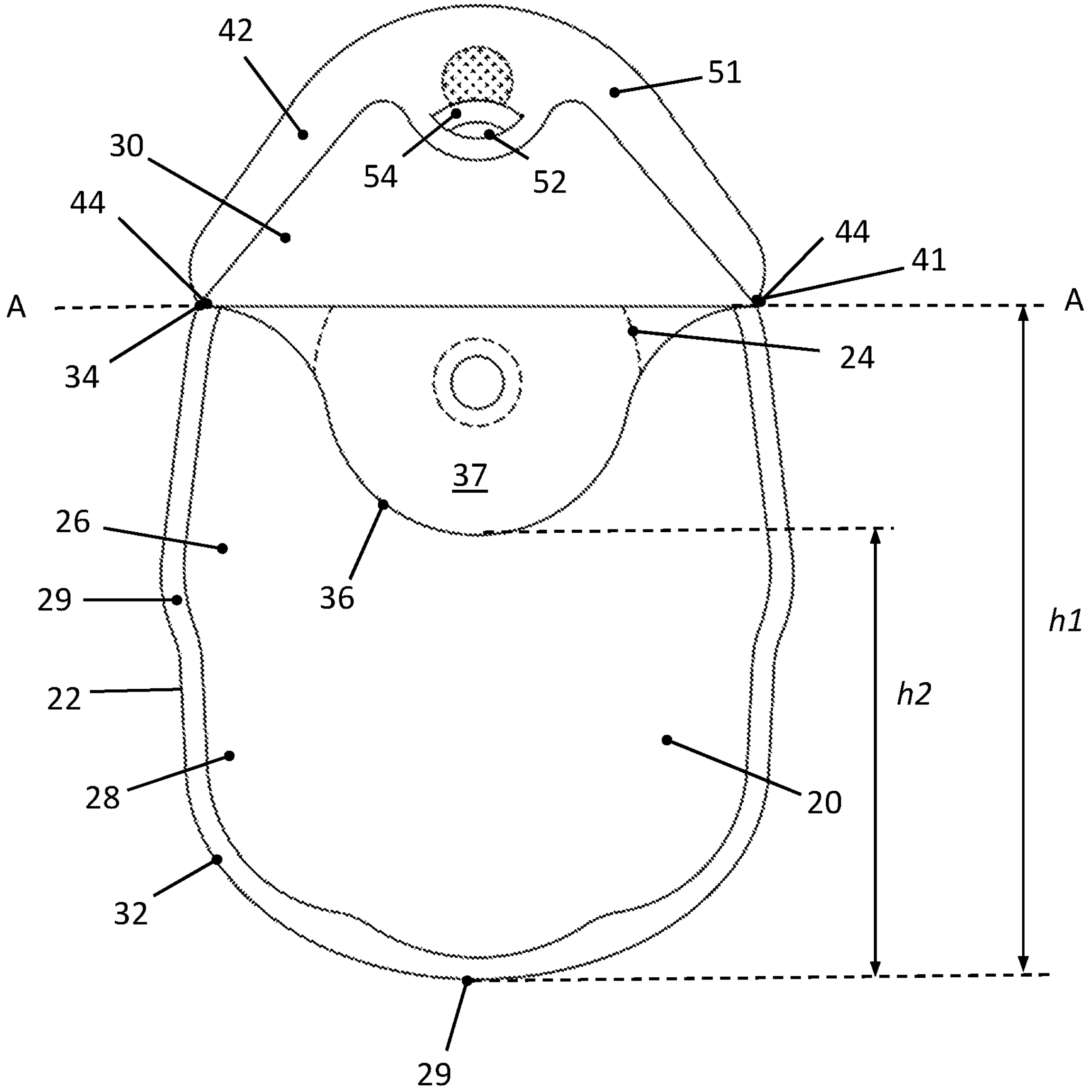
FIG. 2 is a front view of the ostomy pouch of FIG. 1 with the flap in the open configuration.

As shown in FIG. 2, the pouch 1 includes a cover 20 for covering the collecting bag 2. The cover 20 is formed from a lightweight comfort fabric, and preferably a woven material that is bio-sensitive to avoid skin irritation. The cover material may for example be formed from polyethylene, polypropylene or polyester fibres. The cover 20 includes a rear panel 22 arranged at the outer surface of the rear wall 4 such that in use it is located between the rear wall 4 and the wearer's skin. The rear panel 22 has a shape conforming to the shape of the collecting bag 2 with the peripheral edge of the rear panel 22 and the peripheral edge of the rear wall 4 being aligned. The rear panel 22 is located between the rear wall 4 and the mounting flange 8. Therefore, the rear panel 22 is provide with an aperture 24 corresponding in size and shape to the outer edge of the bonding region 14 between the rear wall 4 and the mounting flange 8. In this way, mounting flange 8 is able to bond to the rear wall 4 in the bonding region 14 of the rear wall 4 exposed by the aperture 24. The rear panel 22 is bonded to the rear wall 4 of the collecting bag 2 along its peripheral edge by RF or thermal welding, wherein rear wall 4 is caused to melt and partially penetrate the material of the rear panel 22 to bond the rear panel 22 to the rear wall 4. The welding process is controlled such that the plastic material of the rear wall 4 does not penetrate to the outer surface of the rear panel 22, such that the comfort feel of the fabric material at the outer surface is maintained.

The cover 20 further includes a front section 26 comprising a lower panel 28 and an upper panel 30. The lower panel 28 has a peripheral edge 32 that conforms to the shape of the front wall 3. The front panel 22 is bonded to the front wall 3 of the collecting bag 2 along its peripheral edge by RF or thermal welding, with the region of bonding between the front wall 3 and the lower panel 28 defining a bonding seam 29. The front wall 3 is caused to melt and partially penetrate the material of the lower front panel 28 to bond the lower panel 28 to the front wall 3. The welding process is controlled such that the plastic material of the front wall 3 does not penetrate to the outer surface of the lower panel 28.

The upper edge 34 of the lower panel 28 includes a cut away section 36 that is configured to reveal the underlying stoma inlet 10 and bonding region 14 of the mounting flange 8. At the outer edges of lower panel 28 the upper edge 34 extends to a height h1 from the base 29 of the pouch 1. Inboard of the outer edges, the upper edge 34 curves downwardly to form a scalloped, substantially semi-circular cut away having a radius r1 corresponding to the radius of the bonding region 14, and a lowermost point at height h2. The cut away section 36 is aligned with the bonding region 14, with the cut away section 36 defining a viewing window 37 configured such that the bonding region 14 and the stoma inlet 10 are substantially uncovered by the lower panel 28. The bonding region 14 will always be larger than the stoma inlet 10, and therefore ensuring the bonding region 14 is fully visible through the viewing window means the stoma inlet 10 will always be fully visible.

Figure 3:
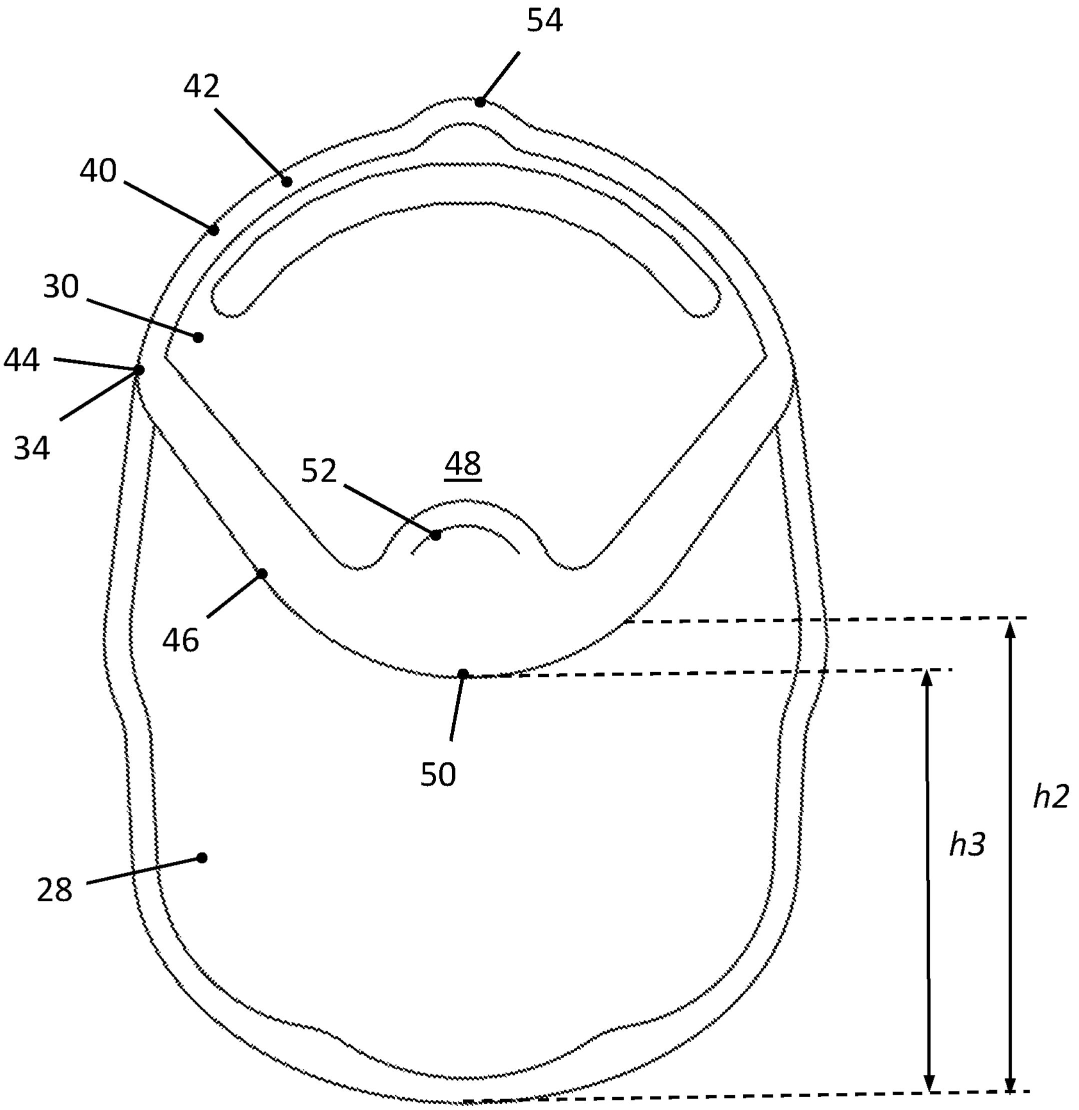
FIG. 3 is a front view of the ostomy pouch of FIG. 1 with the flap in the closed configuration.

The upper panel 30 is arranged above the lower panel 28 and forms a flap for covering the viewing window 36 of the lower panel 28. FIG. 2 shows the closure flap 48 in an open configuration in which the flap 30 is folded upwardly about the fold line A-A to reveal the window 37. In FIG. 3 the upper panel 30 is shown in the closed configuration in which it covers the viewing window 37 of the lower panel 28 and obscures the underlying mounting plate 8 and stoma inlet 10 from view. The upper panel 30 has an outer peripheral edge 40 that corresponds to the shape of the underlying front wall 3. The outer peripheral edge 40 of the upper panel 30 is bonded to the underlying peripheral edge of the front wall 3 by thermal or RF welding, in the same manner as the rear panel 22 is bonded to the rear wall 4, to form a peripheral bonding seam 42. The lower ends 44 of the peripheral bonding seam 42 are adjacent to the upper edge 34 of the lower panel 28 at height h1. The lower edge 46 of the upper panel 30 is free and is not bonded to the front wall 3. The lower edge 46 tapers downwardly an inwardly from either side to form a substantially v-shaped flap 48. The lower end 50 of the flap 48 is located at height h3, lower than height h2, and has a curved form corresponding to, and spaced outwardly of, the curved edge of the cutaway section 36. The flap 48 extends downwardly past the upper edge 34 of the lower panel and overlaps the lower panel 28 to obscure the viewing window 37.

The upper panel 30 is preferably formed as a 3 ply arrangement consisting of front and rear fabric layers and an intermediate polymer film layer that may be the same film material as the collecting bag 2. The three layers are bonded together about their peripheral edges by RF or thermal welding as described above, such that the intermediate layer melts and penetrates both fabric layers. The triple ply thickness of the upper panel 30 provides additional weight that helps maintain the flap 48 in the closed configuration. The lower edge 46 of the upper panel 30 has a bonding region 51 along which the three layers of the flap 48 are bonded. A curved slit 52 is formed in the bonding region 51, inboard of the tip 50 of the flap 48 at the centre of the flap 48. The slit 52 curves upwardly, in a convex manner away from and in the opposing direction to the downward curve of the tip. A locking tab 54 projects from the upper end of the cover 20 at its apex and is laterally aligned with the slit 52. The slit 52 and locking tab 54 are used to hold the flap in the open configuration, as will be described in further detail below. In an alternative arrangement, the slit 52 may be configured such that it receives and hooks over the curved upper edge 40 of the upper panel section 30 such that a portion of the curved upper edge 40 defines the locking tab without the requirement for a pronounced projection.

In alternative embodiments the upper panel 30 may be formed as a 2 ply arrangement comprising a front material layer and rear polymer film layer. The front material layer and polymer film layer are bonded in the same manner as described above for the 3 ply layer. The front material panel provides the same outer comfort layer, while the removal of the rear fabric layer, which would otherwise not be visible when the upper panel is in the lowered position, reduces the material usage and cost.

Referring again to FIG. 2, the lower ends 44 of the bonding region 42 are the lowest points at which the upper panel 20 is secured to the front wall 3. The lower end 44 of the bonding region 42 locate immediately adjacent the upper ends 41 of the bonding region 29 of the lower panel 28. The point at which the lower ends 44 of the bonding region 42 and the upper ends 41 of the bonding region 29 meet defines the outer edges of a fold line A-A about which the flap 48 is folded upwards. The height h1 at which the lower ends 44 are located, and hence the height of the fold line A-A is above the height of the stoma inlet 10. As such, when the flap 48 is folded upwards the stoma opening 10 and the viewing window 36 are uncovered, allowing full visibility of the stoma inlet. The curved shape of the viewing window forms side parts 56 which cover the underlying collecting bag 2 and ensure that only the section of the collecting bag 2 within the viewing window 36 is visible, thereby limiting the extent to which the contents are exposed.

In the open configuration, the slit 52 in the flap 48 is hooked over the upwardly extending locking tab 54 such that the locking tab 54 extends through the slit 52. Hooking the slit 52 over the locking tab 54, the flap is held in the upwardly folded open configuration. The stiffened bonding region 51 maintains the form of the flap 48 when in the upwards open configuration and prevents the tip of the flap 48 from flopping downwards. In other embodiments alternative holding means may be provided. For example, the lower end of the flap 48 may be provided with a Velcro tab, and a corresponding Velcro tab may be affixed at the upper end of the flap 48 and positioned such that it is aligned with the lower Velcro tab when the flap 48 is folded to the open configuration to connect therewith.

In use, when a care giver wishes to inspect the wearer's stoma and/or monitor stoma output or the contents of the pouch the flap 48 is moved to the open configuration by gripping the tip 50 and lifting the flap 48 upwardly. The flap 48 folds about fold line A-A as it is lifted. The flap 48 is then hooked over the tab 54, and the tab 54 inserted into the slit 52 to hold the flap 48 in the open configuration. The care giver is then provided with a full view of the stoma area and can periodically glance at the pouch and monitor the stoma condition and/or pouch contents from a distance, with less frequent close inspections required. If the wearer requires privacy, the flap 48 may be easily lifted and released from the locking tab 54 and folded down to return it to the closed configuration.

Figure 4:
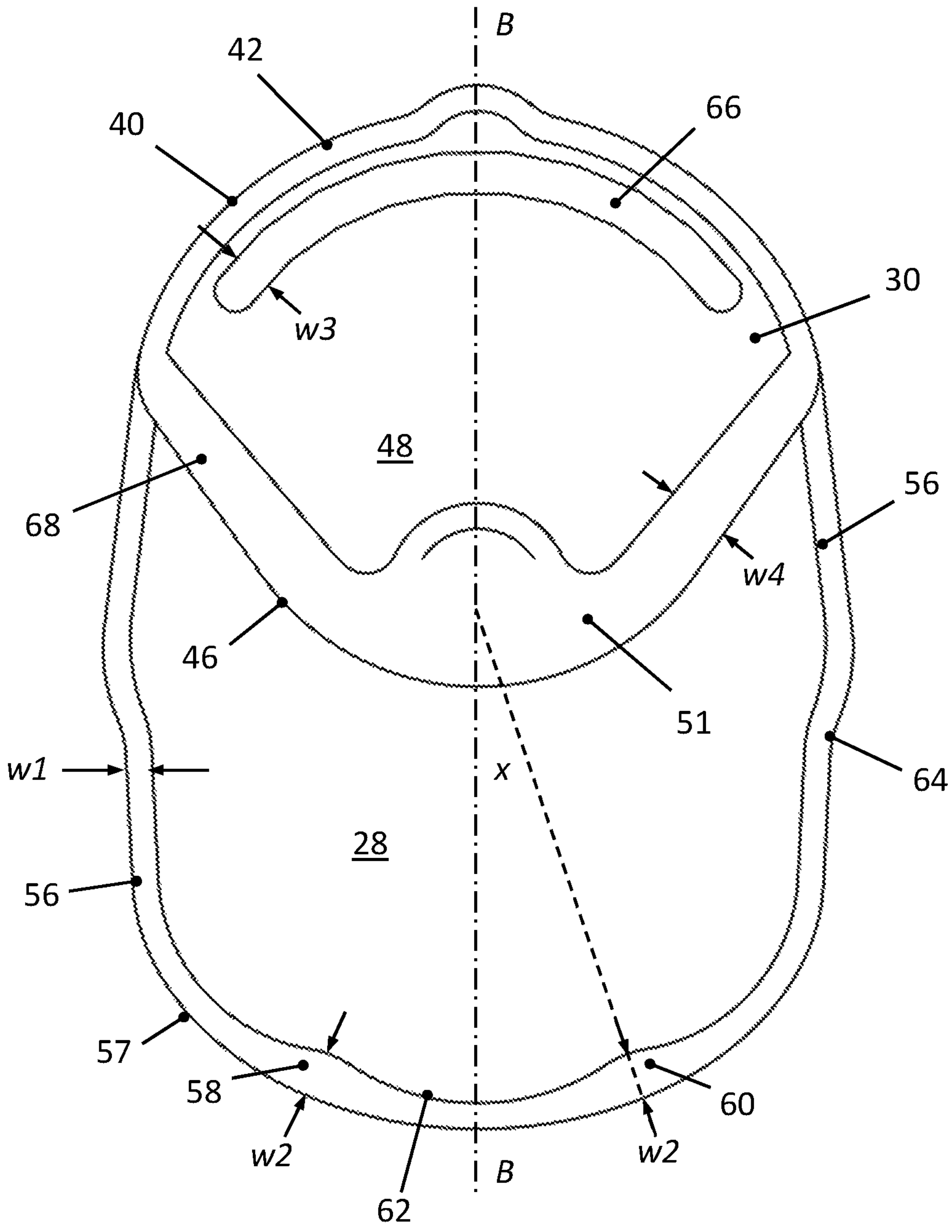
FIG. 4 is a front view of an ostomy pouch according to an embodiment of the present invention.

Referring to FIG. 4, a number of stiffening sections are provided to optimise the shape and performance of the pouch 1 in use, prevent sagging and bulging of the pouch 1, and improve comfort of the pouch 1. The various layers forming the pouch are bonded together in a two-stage process. In a first bonding step the upper panel section 30 is partially bonded. The front and rear fabric layers and intermediate plastic layer of the upper panel section 30 are assembled and are bonded together along the lower edge 46 to form a bonding region 51. The outer peripheral edge 40 of the upper panel section is not bonded in the first bonding step. The partially bonded upper panel section 30 is then assembled together with the remaining elements of the pouch 1 in a layered arrangement. The rear wall 4 of the collecting bag 2 is firstly laid on the lower panel section 28. The front wall 3 is then laid on the rear wall 4. Finally, the upper panel section 30 and the lower panel 28 and laid on the front wall 3. The layered assembly is then bonded around the entire peripheral edge, forming a peripheral bonding region 56, which includes the lower bonding seam 41 and upper bonding seam 42. Bonding is preferably achieved by RF welding although other methods may be used.

The peripheral bonding region 56 extending around the periphery of the pouch 1 is formed having a first width w1. The width w1 is selected to ensure a robust bond and seal between the layers forming the pouch 1. The bonding region 56 includes first and second strengthening zones 58 located at the lower end of the pouch 1 along the curved lower edge 57. The strengthening regions 58 comprise lobes formed by undulations in the bonding region 56 whereby the width of the bonding region is locally increased to a width w2, greater than width w1. As such, the pouch 1 is locally stiffened and reinforced in the region of the strengthening zones 58. The strengthening zones 58 are symmetrically spaced on opposing sides of the longitudinal centreline B-B of the pouch. The strengthening zones 58 are arranged along the curved lower edge at an angle x to the centreline B-B, which is preferably between 10 and 40 degrees and more preferably between 15 and 30 degrees. The strengthening zones 58 only increase in width in the inward direction, that is to say inwardly towards the collection volume of the collecting bag. As such, the outer peripheral edge of the bonding region 56 maintains the curved form of the pouch 1 at the strengthening zones 58. At the inner edge of the bonding region 56, the strengthening zones 58 symmetrically curve gradually inwards from the width w1 to a curved peak defining the maximum width and then curve back outwards to the width w1. The strengthening zones therefore have an undulating, wave-like form and face substantially upwardly away from the lower end of the bag towards the upper end. A concavely curved 'valley' or 'bowl' region 62 is formed between the two convex strengthening zones 58.

In use, as the collecting bag 2 fills, the strengthening zones 58 provide increased stiffness to the lower edge 57, helping it to maintain its form and resist buckling. As the collecting bag 2 continues to fill, the contents are channelled to the centre by the concave valley region 62 formed by the strengthening zones 58. As such, the centre of mass of the load is maintained along the centreline B-B, which prevents uneven distribution of the load across the mounting plate 8. As the collecting bag 2 fills further, the inwardly curved form of the strengthening zones 58 causes the seam defined by the bonding region 56 to kink forwardly, away from the wearer, thereby preventing uncomfortable contact with the stiff seam. The lower end of the pouch 1 is also narrower than the upper end of the pouch 1, with a narrowed waist section 64 being defined at the transition between upper end lower ends. The waist section 64 pinches inwards as the collecting bag 2 fills, further assisting in channelling the contents to the centre of the collecting bag 2.

A third strengthening zone 66 is provided at the upper end of the upper panel section 30. The third strengthening zone 66 conforms to the shape of the upper peripheral edge of the upper panel 30. The third strengthening zone 66 is substantially C-shaped, having a convexly curved strip arranged parallel with the upper peripheral bonding seam 42 and the peripheral edge 40 of the upper panel section 30. In the arrangement of FIG. 4 the third strengthening zone 66 is spaced inwardly from the peripheral bonding seam 42 and is arranged symmetrically about the centreline B-B. The third strengthening zone 66 has a width w3 that is greater than the width w1 of the peripheral bonding seam 56, and the width w3 is preferably constant along the length of the third strengthening zone 66. The third strengthening zone 66 is formed on the upper panel section 30 during the first bonding operation, simultaneous with the formation of the bonding region 51. The third strengthening zone 66 is formed by bonding of the upper and lower layers of the upper panel section 30 to the intermediate layer between them. This bonding step is performed in the same step as the formation of the bonding region 51, prior to the pouch being assembled. The curved third strengthening zone 66 stiffens the upper end of the pouch 1 and helps maintain the form of the upper end of the pouch 1 as the collecting bag 2 fills and resists the sagging force applied by the increasing load. The third strengthening zone 66 therefore helps maintain the form of the pouch 1 and by preventing sagging, folding or kinking of the upper part of the pouch 1 ensures that a profile is maintained that is acceptable to the wearer. That is to say, it prevents the pouch 1 from sagging and bulging outwardly, thereby becoming more pronounced and conspicuous beneath the wearer's clothing.

The upper panel section 30 is further provided with a fourth strengthening zone 68. The fourth strengthening zone 68 is defined by the bonding region 51 along the lower edge 46 of the flap 48, which is formed having a width w4 that is greater than the width w1 of the peripheral bonding seam 56. The fourth strengthening zone 68 stiffens the lower edge 46 of the flap 48 and enables the flap 8 to hold its form when held upwardly in the open configuration, as well as holding its form and preventing creasing in the lowered position to ensure the upper panel 30 remains closed and prevents unwanted exposure of the window. The fourth strengthening zone 68 includes an expended central region 70 at the tip of the flap 48 formed by an upwardly curved portion of the inner edge of the fourth strengthening zone 68. The expended central region 70 accommodates the holding slit 52 and strengthens the area around the slit to prevent this area from buckling when the slit is hooked over the locking tab 54.

Figure 5:
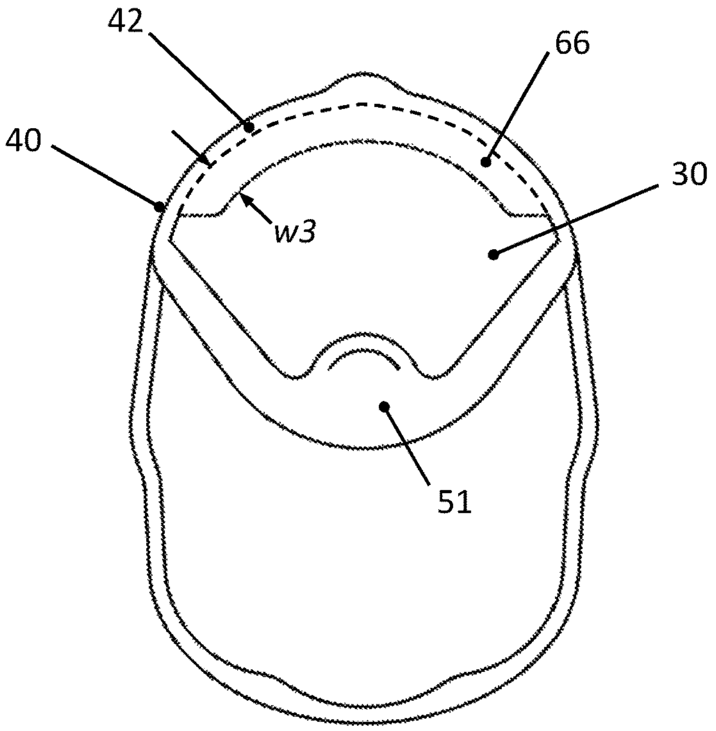
FIG. 5 is a front view of an ostomy pouch according to an alternative embodiment of the present invention.

In an alternative embodiment, as shown in FIG. 5, the third strengthening zone 66 may be arranged so that it adjoins and is integrated with the upper bonding seam 42. In the arrangement of FIG. 5 this is achieved by increasing the width w3 of the third strengthening zone 66 so it extends to the upper bonding seam 42. The third strengthening zone 66 is formed in a first bonding step, and then integrated with the upper bonding seam 42 when the upper bonding seam 42 if formed in the final welding step. The integration of the third strengthening zone 66 and upper bonding seam 42 provides increased stiffening of the upper end of the pouch 1 where additional reinforcement against sagging is required.

Figure 6:
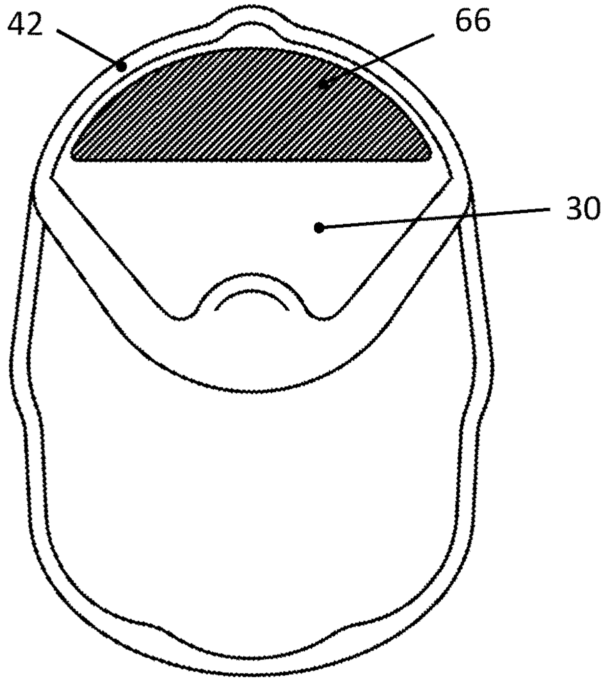
FIG. 6 is a front view of an ostomy pouch according to an alternative embodiment of the present invention having a semi circular strengthening zone on the upper cover section.

FIG. 6 shows an alternative means of providing additional reinforcement. In the arrangement of FIG. 6 the third strengthening zone 66 is formed having a substantially semi-circular shape, with a curved upper edge that conforms to the shape of the upper edge of the pouch 1. The increased area of the third strengthening zone 66 in this embodiment provides additional stiffening to maintain the upper panel 30 in the lowered state.

Figure 7:
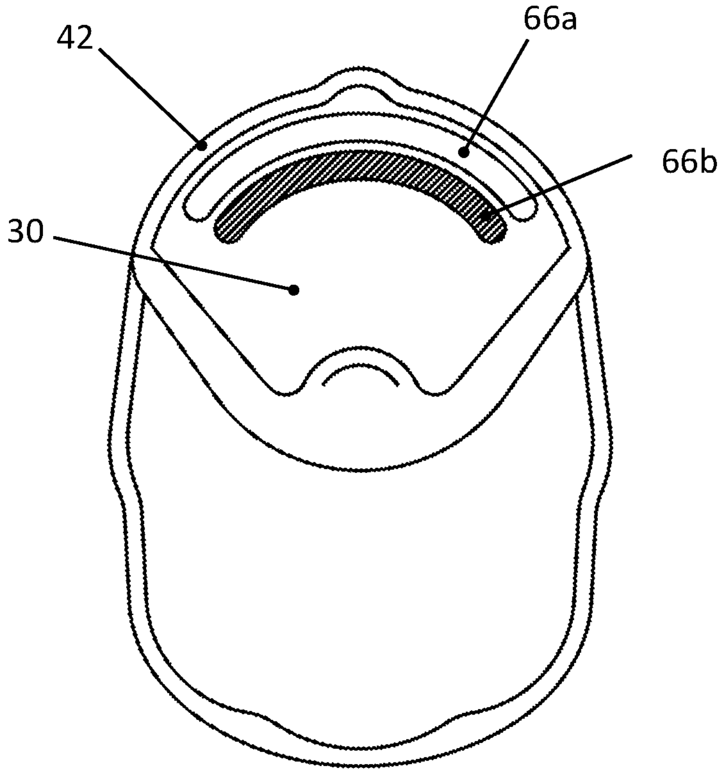
FIG. 7 is a front view of an ostomy pouch according to an a yet further embodiment of the present invention having a plurality of parallel strengthening zones on the upper cover section.

The third strengthening zone 66 of the upper panel 30 may include more than one curved stiffening strip. In the FIG. 7 the third strengthening zone 66 comprises a pair of stiffening strips 66*a* and 66*b* arranged concentrically such that both confirm to the curved shape of the upper edge of the pouch 1. This is an alternative means of increasing the area of the third strengthening zone 66 and strengthening the upper panel 30.

Figure 8:
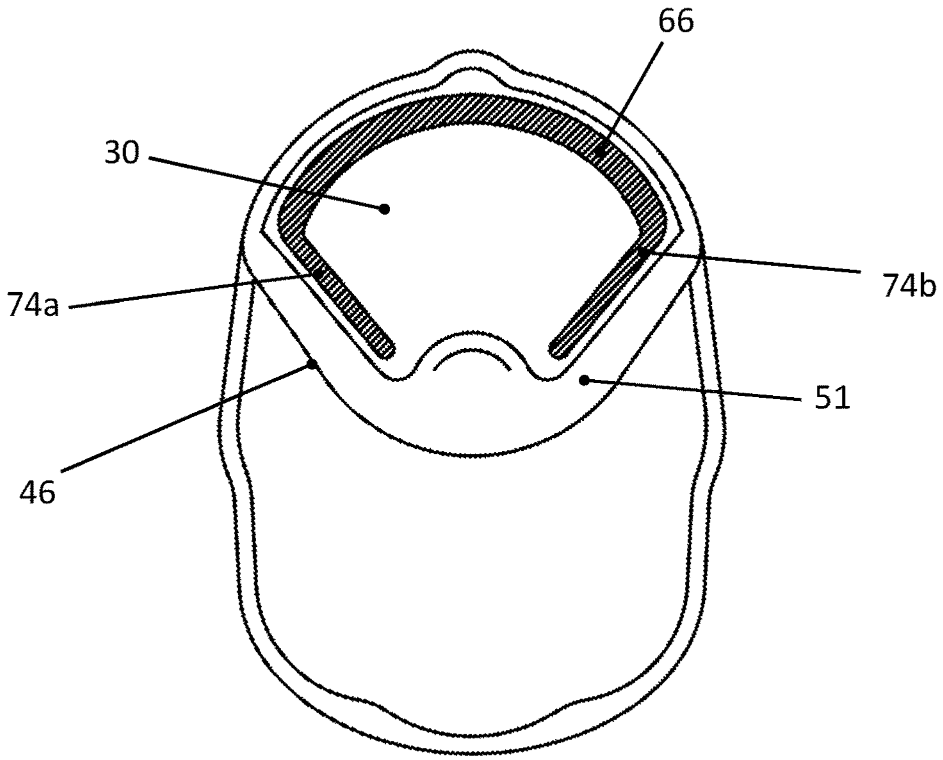
FIG. 8 is a front view of an ostomy pouch according to an alternative embodiment of the present invention having stiffening arms extending from the curved strengthening zone of the upper cover section.
Figure 9:
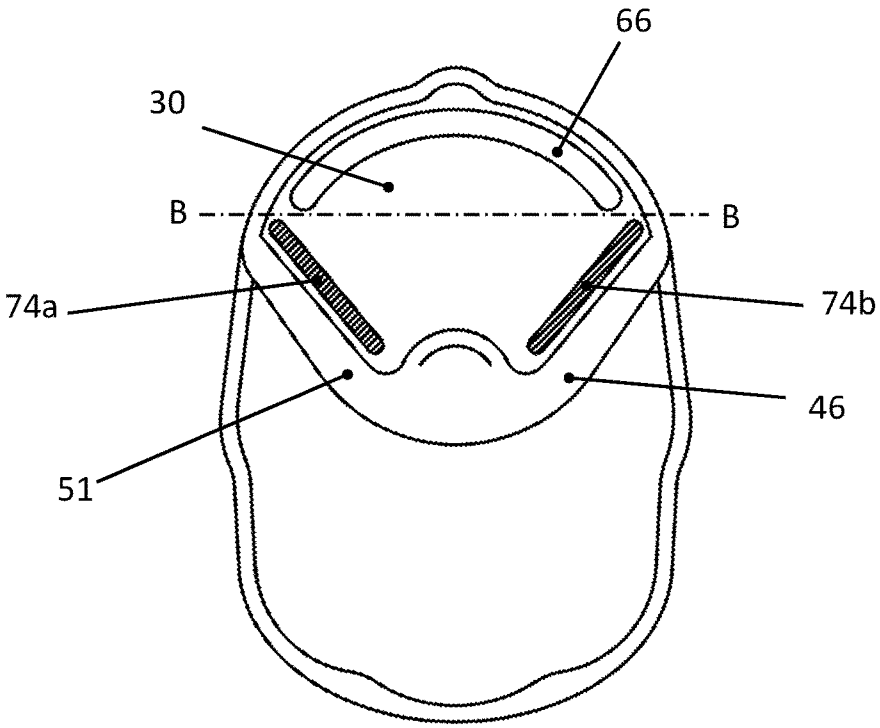
FIG. 9 is a front view of an ostomy pouch according to an alternative embodiment of the present invention in which the stiffening arms are spaced from the curved strengthening zone of the upper cover section.

In the embodiment of FIG. 8, the third strengthening zone 66 includes a curved c-shaped section, and stiffening arms 74*a* and 74*b*. The stiffening arms 74*a* and 74*b* extend downwardly from opposing ends of c-shaped section 66 and are arranged parallel to and spaced inwardly from the lower edge 46 of the upper panel 30. The stiffening arms 74*a* and 74*b* work in conjunction with the second bonding region 51 to increase the stiffness of the lower part of the upper panel 30 and provide structure to prevent creasing in the closed position and support the upper panel 30 to hold its form when in the raised open position. The stiffening arms 74*a* and 74*b* extend directly from the curved strip 66 and across the fold line A-A, and as such may inhibit folding of the upper panel 30 to the open position. To address this, in the embodiment of FIG. 9 the upper ends of the stiffening arms 74*a* and 74*b* are vertically spaced from the ends of the curved strip 72, the gap defined by the vertical spacing being defining a fold line A-A, which enables the upper panel 30 to more effectively fold to the open position.

Figure 10:
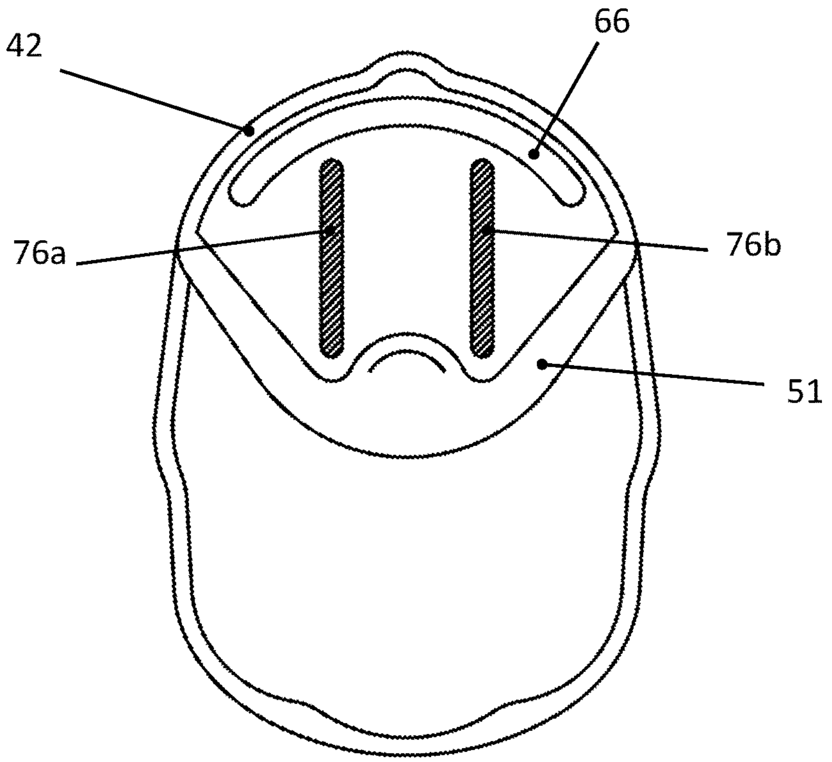
FIG. 10 is a front view of an ostomy pouch according to an alternative embodiment of the present invention having vertical stiffening elements located beneath the curved strengthening zone of the upper cover section.
Figure 11:
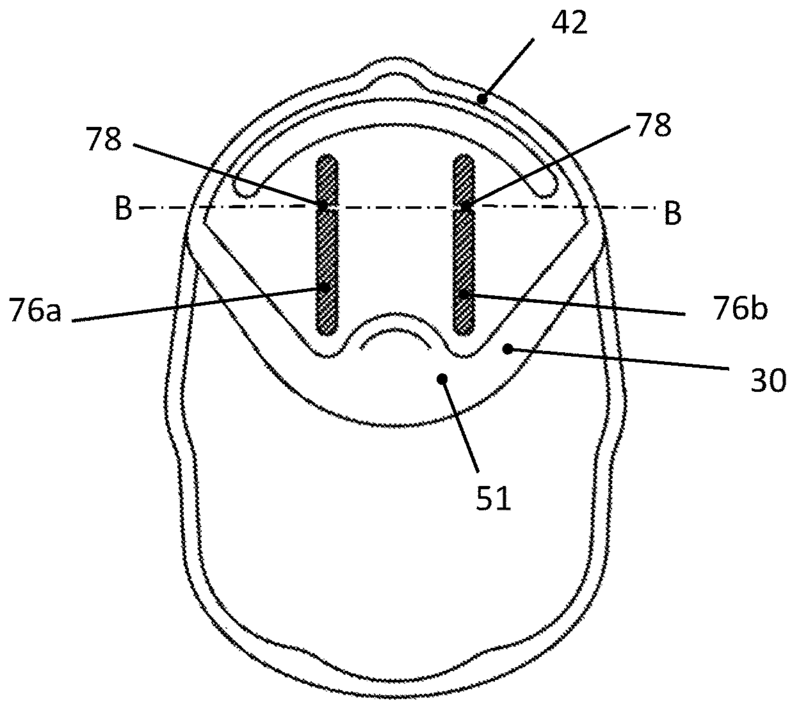
FIG. 11 is a front view of an ostomy pouch according to an alternative embodiment of the present invention having vertical stiffening elements with split lines located along the fold line of the upper cover section.

Alternatively, vertical stiffening strips 76*a* and 76*b* may be provided, as shown in FIG. 10. The stiffening strips 76*a* and 76*b* are arranged vertically in a spaced parallel arrangement, in board of the peripheral bonding seam 42 and lower bonding seam 51. The vertical stiffening strips 76*a* and 76*b* provide structure to the upper panel 30 but may inhibit folding of the upper panel 30 to the open position. To address this, in the embodiment of FIG. 11 each of the vertical stiffening strips 76*a* and 76*b* include a split line 78 arranged to define a fold line B-B. Each split line 78 is a separation or break in the stiffening strips 76*a*, 76*b* that enables the upper panel 30 to fold about the fold line A-A. more effectively.

The invention claimed is:

1. A collecting apparatus for bodily fluids or bodily waste comprising:

a plurality of flexible polymer film layers, at least two of which form a collecting bag for containing bodily fluids or bodily waste, the collecting bag comprising front and rear walls formed from said at least two flexible polymer film layers;

an opening in the rear wall of the collecting bag for receiving bodily fluids or bodily waste;

a flexible material cover at least partially covering the collecting bag and comprising a front part, wherein the front part is arranged on a first side of the collecting bag, and the first side faces forward and away from the user during use;

a peripheral bonding seam extending along at least an upper edge of the collecting apparatus that bonds at least part of the collecting bag and the flexible material cover together; and at least one strengthening element formed at an upper end of the collecting apparatus inwardly of the peripheral bonding seam by a region of bonding, wherein the region of bonding is between one or more of the flexible polymer film layers and the front part of the flexible material cover, and wherein the at least one strengthening element strengthens an upper section of the apparatus to inhibit sagging of the upper section as the collecting bag is filled in use.

2. The collecting apparatus according to claim 1, wherein at least one of the at least one strengthening element has a shape that conforms to the shape of the peripheral bonding seam at the upper end of the collecting apparatus.

3. The collecting apparatus according to claim 2, wherein the upper edge of the collecting apparatus has a convex curved shape and the at least one strengthening element has a correspondingly curved shape.

4. The collecting apparatus according to claim 3, wherein the at least one strengthening element has an elongate arcuate shape.

5. The collecting apparatus according to claim 3, wherein the at least one strengthening element extends parallel to the curved upper edge of the collecting apparatus.

6. The collecting apparatus according to claim 1, wherein the front part of the flexible material cover consists of an upper cover section and a lower cover section, the upper cover section is formed of at least one flexible material layer and at least one flexible polymer film layer that are bonded together to form the at least one strengthening element.

7. The collecting apparatus according to claim 6, wherein at least one of the at least one strengthening element extending across the upper section of the collecting apparatus is spaced inwardly from the peripheral bonding seam such that a gap is defined therebetween that is spanned by an unbonded portion of the flexible material layer and the flexible polymer layer.

8. The collecting apparatus according to claim 6, wherein the lower cover section includes a viewing window through which the opening of the collecting bag is visible and the upper cover section forms a flap that is reconfigurable between a closed configuration in which at least part of the upper cover section covers the viewing window and the opening is obscured, and an open configuration in which the viewing window is uncovered and the opening is visible.

9. The collecting apparatus according to claim 8, wherein the upper cover section comprises an outer flexible material layer and an intermediate flexible polymer film layer located between the outer flexible material layer and the collecting bag, and the at least one strengthening element is formed by regional bonding between the outer flexible material layer and the intermediate flexible polymer film layer.

10. The collecting apparatus according to claim 6, wherein the upper cover section has an outer peripheral edge that is bonded with and forms part of the peripheral bonding seam and a lower edge located inboard of the outer peripheral edge at least part of which extends across the apparatus below the level of the window, wherein the outer flexible material layer and the intermediate polymer film layer are bonded along the lower edge to form a strengthening element that stiffens the lower edge and maintain its form in the open and closed configurations.

11. The collecting apparatus according to claim 9, wherein the upper cover section further comprises an inner flexible material layer located on the opposing side of the intermediate flexible polymer film layer to the outer flexible material layer and the at least one strengthening element is formed by a region of bonding between the outer flexible material layer, the inner flexible material layer, and the intermediate flexible polymer film layer.

12. The collecting apparatus according to claim 10, further comprising a plurality of strengthening elements, wherein the upper cover section has a width extending across the apparatus and a length extending vertically along the apparatus, and at least one of the strengthening elements is an elongate element extending lengthwise along part of the upper cover section inboard of the outer peripheral edge to stiffen the upper cover section and maintain its form in the open and closed configurations.

13. The collecting apparatus according to claim 12, wherein a portion of the upper cover section folds about a lateral fold line to reconfigure the upper cover section between the open and closed configurations and the at least one strengthening element is arranged such that they are not located on or across the fold line.

14. The collecting apparatus according to claim 12, wherein a portion of the upper cover section folds about a lateral fold line to reconfigure the upper cover section between the open and closed configurations and the one or more elongate strengthening elements arranged lengthwise along the upper cover section include a split line or weakened section located at the fold line to facilitate folding of the upper cover section.

15. The collecting apparatus according to claim 14, wherein the upper cover section has a lower edge that is lowermost in the closed configuration and the upper cover section includes a strengthening element located along the lower edge to strengthen the lower edge and maintain the form of the upper cover section in use.

16. The collecting apparatus according to claim 15, wherein the upper cover section includes an inner material panel, an outer flexible material panel, and an intermediate flexible polymer film that are bonded together to form the strengthening element along the lower edge of the upper panel section.

17. The collecting apparatus according to claim 16, wherein the upper cover section includes a flap portion that is reconfigurable between a closed position in which the flap covers an underlying part of the collecting apparatus and an open configuration in which the flap exposes said underlying part, wherein the lower edge forms part of the flap section and the strengthening element extending along the lower edge supports the flap section in the open configuration.

18. A collecting apparatus for bodily fluids or bodily waste comprising:

a collecting bag for containing bodily fluids or bodily waste, the collecting bag comprising front and rear walls formed from a flexible polymer film;

an opening in the rear wall of the collecting bag for receiving bodily fluids or bodily waste;

a flexible material cover at least partially covering the collecting bag, the cover comprising a front part arranged on a first side of the collecting bag that in use faces forward away from the wearer and a rear part on the opposing side of the collecting bag that in use is located between the collecting bag and the wearer;

a peripheral bonding seam along which the front and rear parts of the cover and the front and rear walls of the collecting bag are bonded together; and one or more strengthening elements arranged at a lower end of the collecting apparatus and having at least a portion thereof located inboard of the peripheral bonding seam, wherein the front and rear parts of the cover and the front and rear walls of the collecting bag are bonded together to form the one or more strengthening elements for providing the collecting apparatus with structural reinforcement, wherein the collecting apparatus includes a longitudinal central axis extending along its length and the one or more strengthening elements comprise a first strengthening element arranged at the periphery of the collecting apparatus that is integrally formed as part of the peripheral bonding seam, wherein the peripheral bonding seam has a first width w1 and the first strengthening element has a width w2 that is greater than the width w1 and is arranged such that a portion the first strengthening element extends inwardly of the peripheral bonding seam, and a second strengthening element arranged at the periphery of the pouch that is integrally formed as part of the peripheral bonding seam, wherein the second strengthening element has a width w2 and is arranged such that a portion the second strengthening element extends inwardly of the peripheral bonding seam, wherein the first and second strengthening elements are arranged at the lower end of the collecting apparatus on opposing sides of the longitudinal central axis.

19. The collecting apparatus according to claim 18, wherein the first and second strengthening elements have a curved profile defining lobes extending from the peripheral bonding seam;

the first and second strengthening elements have a symmetrically curved profile;

a curved valley section being defined between the first and second strengthening elements that is at least partially formed by curved edges of the first and second strengthening elements; and the collecting apparatus having a curved lower edge and the first and second strengthening elements being located along the curved lower edge.

20. The collecting apparatus according to claim 1, wherein a portion of the at least one strengthening element is formed above the opening.

* * * * *